United States Patent [19]

Lucas

[11] Patent Number: 4,975,645

[45] Date of Patent: Dec. 4, 1990

[54] IMPEDANCE CROSS CORRELATION LOGGING TOOL FOR TWO PHASE FLOW MEASUREMENT

[75] Inventor: Gary Lucas, Ely, England

[73] Assignee: Schlumberger Technology Corporation, Houston, Tex.

[21] Appl. No.: 440,008

[22] Filed: Nov. 21, 1989

[30] Foreign Application Priority Data

Dec. 3, 1988 [GB] United Kingdom ............... 8828271

[51] Int. Cl.$^5$ .................. G01V 3/18; G01R 27/26; G01F 1/64; G01F 1/74
[52] U.S. Cl. .................. 324/324; 73/61.1 R; 73/861.04; 324/355; 324/663; 324/686
[58] Field of Search .......... 324/324, 325, 333, 355, 324/366, 371, 373, 663, 664, 665, 686–690; 73/61 R, 61.1 R, 155, 861.04

[56] References Cited

U.S. PATENT DOCUMENTS

| | | | |
|---|---|---|---|
| 2,852,734 | 9/1958 | Josendal et al. | 324/325 |
| 3,279,249 | 10/1966 | Tocanne | 324/324 X |
| 3,437,924 | 4/1969 | Tocanne | 324/324 X |
| 3,635,082 | 1/1972 | Prellwitz et al. | |
| 4,074,184 | 2/1978 | Dechene et al. | 324/603 X |
| 4,509,366 | 4/1985 | Matsushita et al. | |
| 4,713,603 | 12/1987 | Thorn | |
| 4,751,842 | 6/1988 | Ekrann et al. | |

FOREIGN PATENT DOCUMENTS 685727 5/1964 Canada .................. 324/373
308004 6/1988 European Pat. Off. .

OTHER PUBLICATIONS

"Capacitance Transducers for Concentration Measurement in Multi-Component Flow Processes", 3rd International Conference on Multi-Phase Flow, The Hague, Netherlands, 18-20 May, 1987, by S. M. Huang et al.

*Primary Examiner*—Gerard R. Strecker
*Attorney, Agent, or Firm*—John J. Ryberg; Henri Dupont

[57] ABSTRACT

The logging tool comprises a gas void fraction measurement section (37) consisting of a first set (37) of eight longitudinal electrodes (38) extending parallel to the longitudinal axis of the tool and positioned and regularly spaced around said longitudinal axis, a sleeve (40) made of dielectric material and located in contact and around the electrodes for obtaining an electric field pattern distributed essentially radially between the electrodes and the wall (12) of the borehole facing the electrodes (38), a centralizer (32) for substantially centralizing the tool in the borehole, and a circuit means (69-115) for measuring sequentially the capacitance between two adjacent electrodes for each pair of electrodes, said capacitance being characteristic of the gas void fraction of the fluid flowing in the wellbore. The logging tool comprises in addition a cross correlation gas velocity measurement section (28) which includes a second (48) and a third (50) set of electrodes.

17 Claims, 6 Drawing Sheets

IMPEDANCE CROSS CORRELATION LOGGING TOOL FOR TWO PHASE FLOW MEASUREMENT

The present invention relates to a logging tool for use in a borehole for determining at least one characteristic of the discontinuous phase of a two-phase fluid circulating in the borehole around the logging tool. The tool can be used to measure the volume fraction or the volume flow rate of the discontinuous or dispersed phase in oil/gas flows, the oil being the continuous phase and gas being the discontinuous phase. The mass flow rate of the discontinuous phase is derived from the volume flow rate. Capacitance measurement of the flow is made and therefore the continuous phase is non-conductive.

The parameter which is important to determine in two-phase flow is the mass flow rate of each phase. One way to determine the mass flow rate of one phase is to determine the volume fraction on one hand and the velocity of the phase on the other hand. By volume fraction, or void fraction, it is meant the percentage, in volume, of the discontinuous phase present in the fluid, at a certain time. Several methods have been used to measure the volume fraction of the discontinuous phase, one of them consisting in measuring the capacitance of the fluid, the continuous phase being non-conductive, between two electrodes. One of the problems associated with such a measurement is that the electrical field between the two electrodes is not uniform. U.S. Pat. No. 4,713,603 describes an apparatus in which a homogeneous electric field is maintained between the two electrodes, by surrounding them by a third electrode maintained at a predetermined potential. The fluid is passed between the two plate electrodes and the changes in capacitance between the two plate electrodes is measured. From this measurement the fraction of gas in the fluid is determined.

Another problem associated with capacitance flow meter comes from the non-uniformity of the distribution of the discontinuous phase in cross-section of the flow meter. This is particularly serious when measurements have to be made in wellbores which are sometimes deviated from the vertical. An attempt has been made in our GB patent application No. 87 21858 filed on Sept. 17, 1987, to obtain a uniform sensitivity of the measurement in a cross-section of the flow meter so that the measured value of the capacitance is independent on the position of the discontinuous phase, such as a bubble, in a cross-section of the flow.

To minimise the influence of the flow pattern distribution, a new capacitance flow imaging system has been proposed at the Third International Conference on Multi-Phase Flow, held in the Hague, Netherlands, on May 18-20, 1987. The corresponding paper entitled "Capacitance transducers for concentration measurement in multi-component flow processes", has been published by BHRA, the Fluid Engineering Centre, Cranfield, Bedford, MK430AJ, England, 1987. In accordance with these flow imaging techniques, used for example to visualise the component distribution in multi-component flow pipelines, capacitance measurement is made between pairs of electrodes surrounding the pipe into which the fluid flows so as to obtain real time images of the two-phase flow in one section of the pipe.

A method, much less elaborate than the preceding one, is proposed in U.S. Pat. No. 4,751,842 for measuring the multi-phase distribution within a petroleum stream flowing in a pipe.

Turning to the measurement of the velocity of the discontinuous phase of the two-phase flow, a known method consists in using two electrodes located in the pipe and separated by a known distance, one upstream and the other downstream. The discontinuous phase flowing through the electrodes produces a change in capacitance. By monitoring the time of occurrence of this change in capacitance in the two electrodes, the velocity of the dispersed phase is determined. The combination of void fraction and velocity measurement in order to determine the mass flow rate of two-phase flow fluid has already been proposed in U.S. Pat. No. 4,509,366.

In the devices of the prior art, the fluid to be monitored flows between electrodes. This kind of structure is not appropriate for a logging tool which is lowered into a borehole.

The present invention proposes a logging tool for determining at least one characteristic, such as the void fraction or the mass flow rate, of the discontinuous phase of two-phase fluid circulating in the borehole around the logging tool. Valid measurement can be made even in a borehole deviated from the vertical and with an accuracy which has not been obtained so far.

The logging tool of the invention has a substantially cylindrical shape with a longitudinal axis and comprises at least one set of at least three longitudinal electrodes extending parallel to the longitudinal axis of the tool and positioned and regularly spaced around said longitudinal axis, means for obtaining an electric field pattern distributed essentially radially between the electrodes and the wall of the borehole facing the electrodes, means for substantially centralizing the tool in the borehole, means for measuring sequentially the capacitance between two adjacent electrodes for each pair of electrodes, said one characteristic of the discontinuous phase of the fluid being derived from the capacitance measurement of each pair of electrodes.

A cylindrical sleeve made of dielectric material and located in contact and around the electrodes is preferably used for obtaining an electric field pattern distributed essentially radially between the electrodes and the wall of the borehole facing the electrodes. Ribs extending radially from the centre body of the tool and connected to the earth potential, can also be used between adjacent electrodes so as to improve the electric field pattern.

According to a preferred embodiment, the logging tool comprises a first set of electrodes so as to derive the volume fraction of the discontinuous phase of the fluid, a second and a third identical set of electrodes, the number of electrodes in the second and third set being equal to the number of electrodes in the first set of electrodes and the electrodes of the first, second and third sets being disposed around the longitudinal axis of the tool in the same manner so that one electrode in each set has a corresponding electrode in each of the two other sets aligned on the same generatrix of the tool; the capacitance measurement of one pair of electrodes of the second set being correlated with the capacitance measurement of the corresponding pair of electrodes of the third set, so as to determine the flow velocity of the discontinuous phase of the fluid.

Preferably, the volume fraction measured with each pair of electrodes of the first set is combined with the flow velocity measured with the corresponding pair of electrodes of the second and third set, so as to derive the volume flow rate of the discontinuous phase of the fluid for each flow sector in the borehole corresponding to said pairs of electrodes.

The overall volume flow rate of the discontinuous phase is also determined from the mean value of the volume flow rates determined in all the flow sectors.

Embodiments of the present invention will now be described by way of examples with reference to the accompanying drawings, in which.

Figure 1:
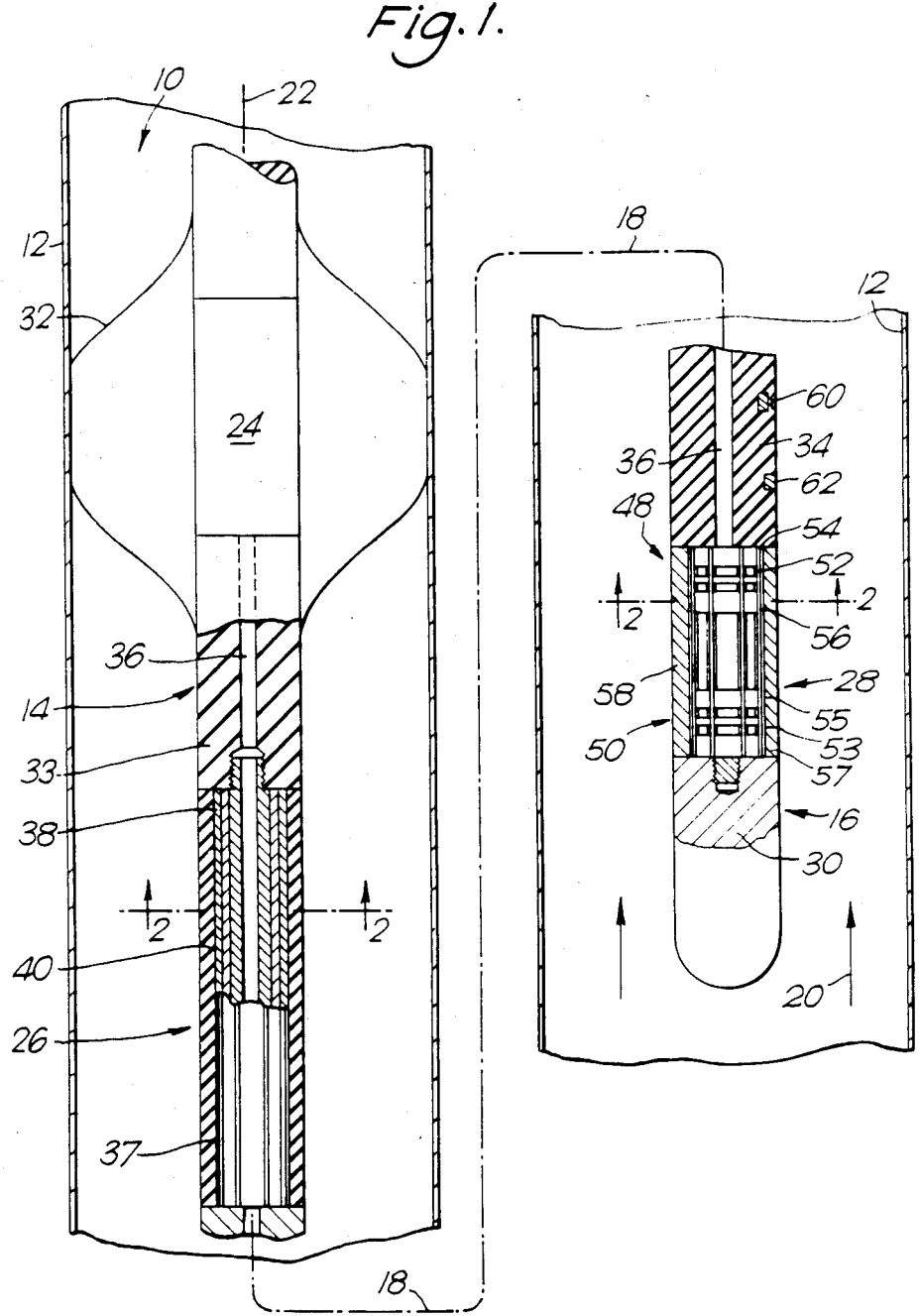
FIG. 1 represents schematically a first embodiment of an impedance cross correlation logging tool in accordance with the invention.
Figure 2:
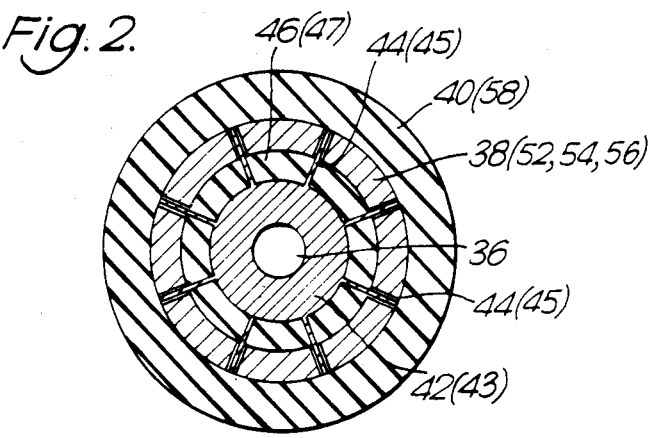
FIG. 2 is a section of the tool of FIG. 1 along the lines 2—2.

The impedance cross correlation logging tool shown in FIGS. 1 and 2 is suspended in the well bore 10 which has been consolidated with the casing 12. The tool is shown in two parts 14 and 16, the dotted lines 18 displaying the way to connect end to end the two parts 14 and 16. The borehole 10 is part of an hydrocarbon well producing a two phase mixture of oil and gas, the oil being the continuous phase—electrically non conductive—and the gas being the discontinuous or dispersed phase. The gas/oil fluid circulates in the borehole from bottom to the surface as indicated by the arrows 20. The logging tool is lowered from the surface with an electrical cable 22 connected at the upper extremity of the tool (not represented). The cable is electrically connected to the electronic section 24 of the tool which comprises the circuits shown in FIGS. 4 and 5. The tool has a cylindrical shape and has therefore a longitudinal axis (in alignment with the cable 22 and in the middle of the duct 36). The tool is basically made of two sections, a volume (or void) fraction measurement section 26 and a cross correlation gas velocity measurement section 28. In addition, the logging tool comprises a nose 30 fixed at its lower extremity. The tool is centred in the borehole with a stabiliser 32. The electronic section 24, the void fraction measurement section 26 and the velocity measurement section 28 are separated by sections 33 and 34 which are hollow rigid cylinders made of a non conductive material, such as Nylon for example. Running through the centre of the logging tool is a wiring duct 36 along which pass screened electrical cables connecting the electrodes of the measurement sections 26 and 28 and the sensors 60 and 62 to the electronic section 24.

The void fraction measurement section 26 comprises a first set 37 of eight, 45° spaced, electrodes 38, each electrode having an axial length of 0.5 meter. A dielectric sleeve 40 made from an appropriate dielectric material of relative permitivity of about 2.1, such as Teflon for example, is placed around the electrodes 38. A hollow metallic centre body 42 extends along the longitudinal axis of the void fraction measurement section. This centre body has eight ribs 44 extending radially between the electrodes 38 but not in contact with them. The ribs are used as guard electrodes and therefore the centre body 42 and the ribs 44 are preferentially placed at the earth potential. Between the centre body 42 and the electrodes 38 are wedges 46 made of a non conductive material. These wedges isolate electrically the electrodes from the centre body.

In addition to the first set 37 of electrodes 38 of the void fraction measurement section, the logging tool comprises a second and a third identical set 48 and 50 of 45° spaced electrodes which form the cross correlation velocity measurement section 28. On FIG. 2, the reference numerals related to the velocity measurement section 28 have been indicated in brackets. Each set 48 or 50 includes eight measuring electrodes respectively 52 or 53. The right measuring electrodes of each set are by eight guard electrodes respectively 54 and 56 or 55 and 57. These electrodes are assembled around the centre body 43 identical to the centre body 42 in the same way as the first set of electrodes of the void fraction measurement section. There are therefore, as shown on FIG. 2, wedges 47 located between the centre body 43 and the electrodes 52 to 57. In addition, ribs 45 extend radially from the centre body 43 in between the individual electrodes 52 and 53. A dielectric sleeve 58 made of an appropriate dielectric material of relative permitivity of about 2.1, such as Teflon for example, is placed around the second and third sets of electrodes 48 and 50. All electrodes of both measurement sections are relatively thin (about 1 millimetre thick) and regularly spaced around the longitudinal axis of the tool and are aligned along the same generatrices of the tool. In other words, at one electrode 38 of the first set correspond two electrodes 52 and 53 (and their guard electrodes 54, 56, 55, 57) aligned along the same generatrix of the tool.

The logging tool also comprises a pressure transducer 60 and a temperature transducer 68 which are connected to the electronic section 24 by electrical wires passing through the ducts 36.

The upper measurement section of the tool, section 26, is used to measure the gas volume fraction or gas void fraction of the two phase fluid gas/oil flowing from the underground producing formation up to the surface, and therefore flowing around the tool. The method consists in measuring sequentially the capacitance of pairs of adjacent electrodes 38. For that purpose, one electrode of two adjacent electrodes is driven at some excitation potential $V(t)$, the other electrode being at virtual earth potential (the measuring of it being explained hereafter), and the remaining electrodes of the measurement section being at true earth potential. Using the detection circuit 69 of FIG. 4, the capacitance between the two considered adjacent electrodes is measured. This measured value of capacitance is dependent upon the relative permittivity of the fluid in the sector 64 (FIG. 3) of the borehole located in front of the two electrodes. The relative permittivity of an oil/gas mixture is related to the gas void fraction. It follows that the measured capacitance between two adjacent electrodes 38 is characteristic of the gas void fraction in the corresponding sector of the borehole.

Figure 3:
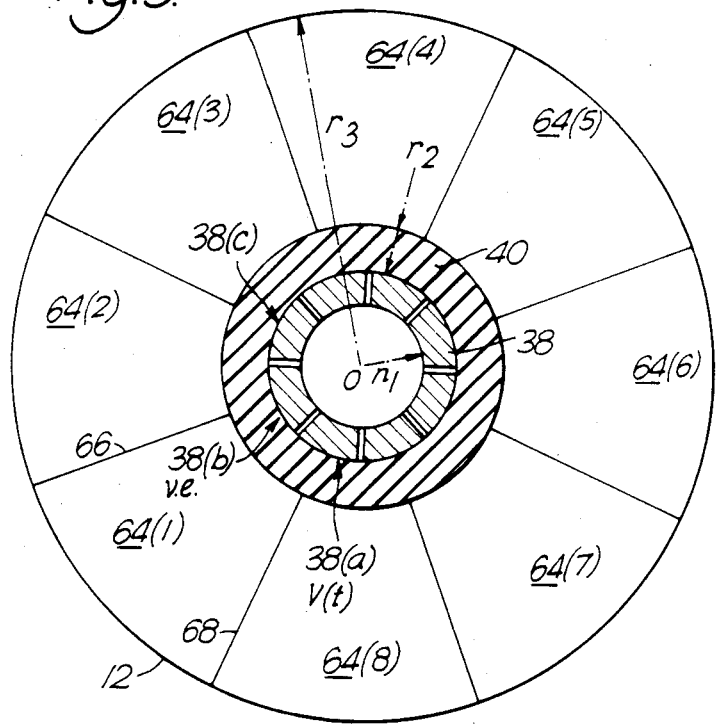
FIG. 3 is a representation of the division of the flow annulus into eight sectors.

FIG. 3 is a simplified representation of a section of the borehole wherein the logging tool is located. The tool is only represented by the electrodes 38 and the dielectric sleeve 40. The annular space between the tool and the well casing 12 has been divided in eight identical sectors 64(1) to 64(8). As an example, the sector 64(1) is delimited by the two radial planes 66 and 68 containing the centre axis O of the tool and passing in the middle of the electrodes 38(a) and (b), the outer wall of the dielectric sleeve 40 and the casing 12. The idealized split of the flow annulus into eight sectors 64 has been demonstrated to be a good and sufficiently accurate representation of the effective areas of sensitivity of the capacitance measurement between two adjacent electrodes. Let us consider two adjacent electrodes, electrode 38(a) driven at an excitation potential V(t) and electrode 38(b) at virtual earth v.e., the other electrodes being at true earth. By measuring the capacitance between the two electrodes 38(a) and (b), a determination of the gas volume fraction of the fluid flowing into the sector 64(1) can be made. Then electrode 38(b) is driven at the excitation potential V(t), the adjacent electrode 38(c) being at virtual earth and all the other electrodes being at true earth potential. By measuring the capacitance between the two electrodes 38(b) and (c), a determination of the gas void fraction of the fluid flowing into the sector 64(2) can be made. In a sequential manner, each of the eight electrodes 38 is driven at the excitation potential V(t) and therefore a measurement of the gas void fraction in each sector 64 is made. Using the multiplexor 115 of FIG. 5, the potentials applied to the electrodes 38 can be switched sequentially, enabling the gas void fraction in the sectors 64(1) to 64(8) to be measured. By combining these individual measurements, an estimate of the overall gas void fraction of the flow can be obtained.

The purpose of the dielectric sleeve 40 is to increase the depth of investigation, into the flow, of the electrostatic field generated by the electrodes. By using the dielectric sleeve, the electrical lines of the electric field generated by the excitation potential V(t) are substantially radial, from the electrodes to the casing, and do not bend and flow between two adjacent electrodes. With the dielectric sleeve, the electrostatic field sensitivity to a discontinuity, such as a bubble of gas in the fluid, is relatively uniform in all the sector areas. The dielectric sleeve 40 (or 58) is made of solid dielectric material, the relative permittivity of which being substantially identical to that of the continuous phase (i.e., crude oil). In addition, it has been shown that an appropriate dielectric sleeve thickness $r_2$ (FIG. 3) is such that the ratio $r_1/r_2$ has a value comprised between 0.58 and 0.66, the preferred value being 0.62, where $r_1$ is the radius of the electrodes 38 i.e., the distance between the electrodes to the center O corresponding to the longitudinal axis of the tool. The preferred sleeve thickness was theoretically obtained for the case where the ratio of the electrode radius $r_1$ to the well casing radius $r_3$ was such that $r_1/r_3$ was equal to 0.26. This corresponds to a 4.3 centimeter diameter tool in a casing of 10.3 centrimeter internal diameter.

The purpose of the ribs 44 of the centre body 42 is to prevent the electrical current to flow between two adjacent electrodes. The ribs 44 act as guard electrodes and are therefore usually connected to the earth potential.

Figure 4:
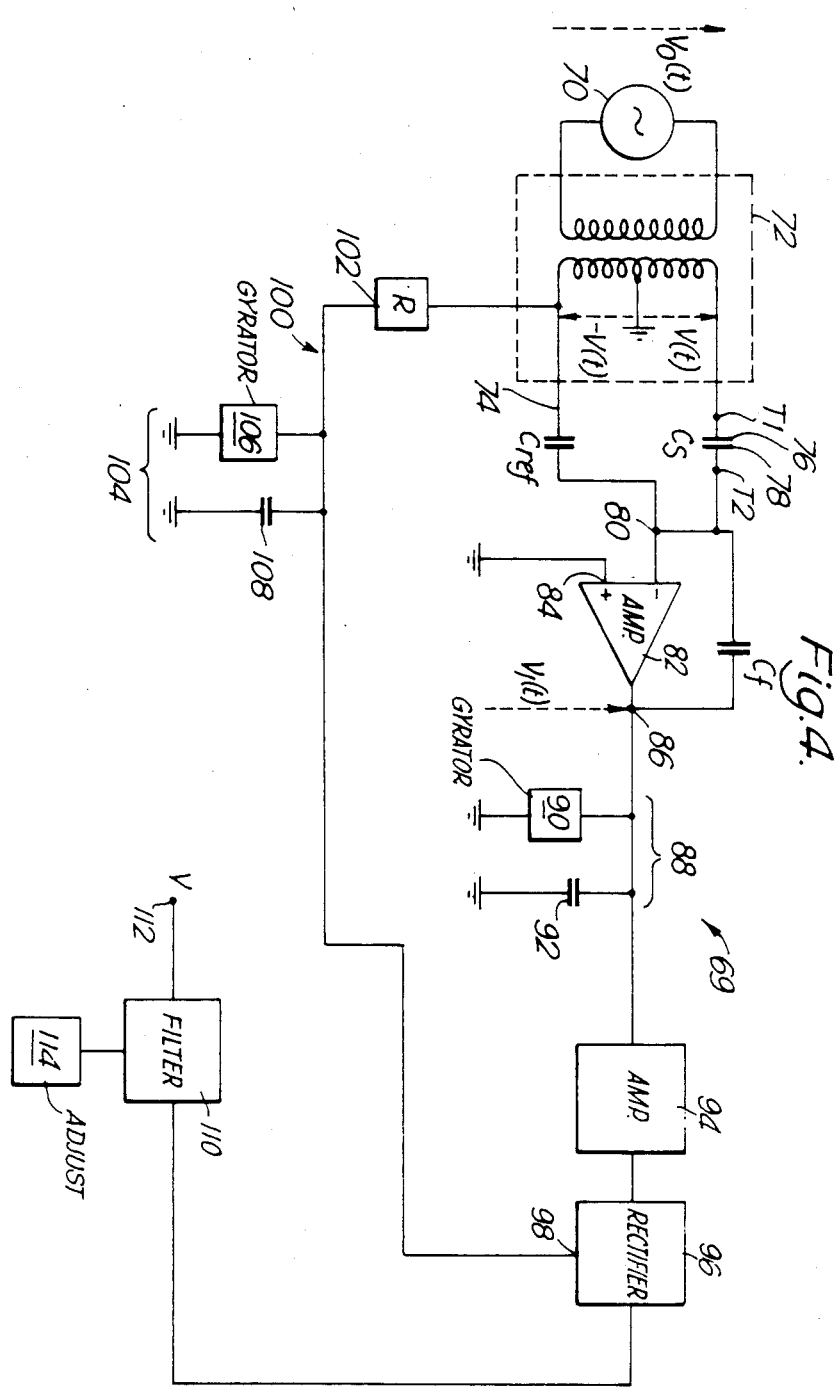
FIG. 4 is a block diagram of the circuitry used for measuring the capacitance between two electrodes of the void fraction and flow velocity sensors.

FIG. 4 is the block diagram of the circuit 69 used for measuring the capacitance $C_s$ between two adjacent electrodes in both the void fraction measurement section 26 and the flow velocity measurement section 28. The logging tool could therefore comprise only one circuit 69 shown on FIG. 4 for the capacitance measurement between two successive electrodes of the three sets 37, 48 and 50 of electrodes. However, the tool comprises three identical circuits 69 of FIG. 4 and three multiplexors 115 (FIG. 5), one circuit 69 and one multiplexer being associated only with one of the three sets of electrodes. The circuit comprises a sine wave generator 70 delivering a potential signal $V_o(t)$ at 10 kilohertz. This signal is applied to a transformer 72 which delivers at its output $T_1$ a signal V(t) and at its output 74 an identical signal $-V(t)$, but of opposite phase. The capacitance $C_s$ to be measured (the capacitance between two successive electrodes) is connected with the multiplexor of FIG. 5, between the two terminals $T_1$ and $T_2$. References 76 and 78 of the capacitance represent the two electrodes, electrode 76 being driven at the potential V(t) and the other electrode 78 being connected at the input 80 of an operational amplifier 82, the other input 84 of the amplifier being connected to earth. $C_f$ is the feedback capacitor of the operational amplifier. Input 80 also receives the signal $-V(t)$ through a reference capacitor $C_{ref}$. The input 80, and therefore the electrode 78, is said to be at virtual earth because the potential difference between inputs 80 and 84 of the amplifier is very small, almost null. The output 86 of the operational amplifier delivers a signal $V_1(t)$ which is equal to $$V_1(t) = \frac{C_s - C_{ref}}{C_f} V(t)$$

Values of the capacitors $C_{ref}$ and $C_f$ and the potential V(t) are known and therefore the signal $V_1(t)$ is a direct measurement of the capacitor $C_s$. The signal $V_1(t)$ is at 10 kilohertz. The remaining part of the circuit aims at delivering a direct current output V proportional to $C_s$. For that purpose, the signal $V_1(t)$ is first filtered at 10 kilohertz by passing through a bandpass filter 88 composed of a gyrator 90, or active inductor, and a capacitor 92. Then the signal at 10 kilohertz is amplified with the ac amplifier 94 and then rectified with a precision rectifier 96. This rectifier is fed with a reference signal in 98, delivered by the reference branch 100 of the circuit. This branch is supplied with the signal $-V(t)$ from the transformer 72. The signal $-V(t)$ passes through a resistance 102 and then a bandpass filter 104 composed of a gyrator 106 and a capacitor 108. The rectified signal delivered by the rectifier 96 is converted into a dc signal by passing through a lowpass filter 110. The output 112 of the circuit delivers a dc signal V proportional to the capacitance $C_s$. A zero adjustment circuit 114 is used to adjust the output signal V of the lowpass filter 110 so that a zero void fraction gives a zero output voltage V.

The measured values of capacitance from each of the three circuits 69 are sent through the cable 22, directly from the electronic section 24 to a data acquisition and processing system at the surface. Such a system can be a computer.

Figure 5:
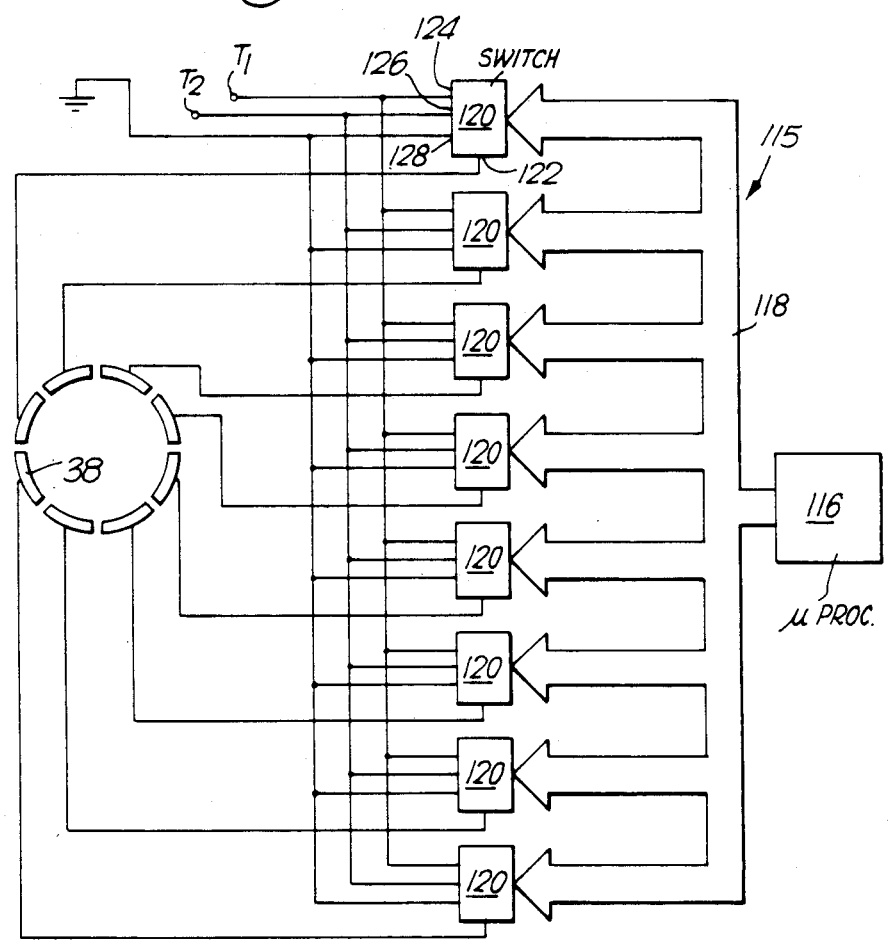
FIG. 5 is a block diagram of the multiplexor used in connection with the circuitry of FIG. 4.

The multiplexor 115 shown on FIG. 5 is used for each circuit 69 to connect each pair of successive electrodes 38 and 52 to the terminals $T_1$ and $T_2$ of FIG. 4 so as to measure the capacitance between the two electrodes connected to $T_1$ and $T_2$. The multiplexor comprises a microprocessor 116, the address bus 118 of which being connected to eight integrated circuits 120. The integrated circuits 120 can be any multiple input analogue switch such as DG528 switch shown in Data Sheet 7477 supplied by the company RS in England. Each electrode 38 is connected to the output 122 of one switch 120. The three inputs 124, 126 and 128 of each switch 120 are connected respectively to terminals $T_1$ and $T_2$ and to the earth potential. The switches 120 are sequentially driven by the microprocessor 116 so that each pair of successive electrodes are sequentially connected to terminals $T_1$ and $T_2$. A controller (not represented) synchronises the working of the microprocessors 116 of the three multiplexors 115.

Figure 6:
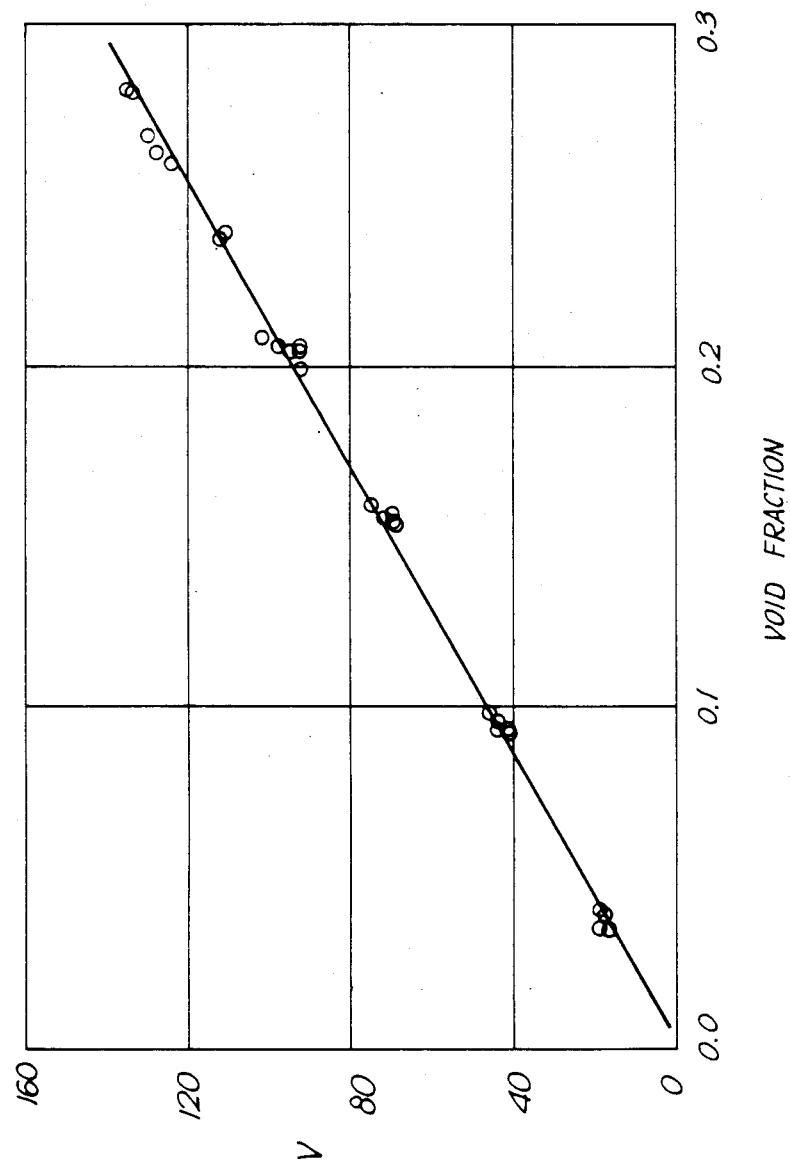
FIG. 6 shows the variation of the output voltage delivered by the circuit of FIG. 4 with the volume fraction, in vertical flow.

FIG. 6 shows the variation of the voltage signal V delivered by the circuit of FIG. 4 for a particular sector 64 of the wellbore annulus as a function of the gas void fraction of the fluid, in a vertical flow. It is clearly apparent that the voltage V is remarkably proportional to the gas void fraction. As a consequence, a way to link the capacitance measurement in each sector with the void fraction values is to calibrate the tool, for example by measuring the capacitance in crude oil (0% void fraction) and in air or gas only (100% void fraction). Intermediate values of void fraction are derived by a linear relationship between 0% and 100% void fraction measurements. Another alternative is by computing the theoretical value of the capacitance of the sectors for predetermined values of void fraction.

Turning now to the cross correlation velocity measurement section 28 of the tool, this section comprises two sets 48 and 50 of electrodes, constituting two flow sensors. Each flow sensor consists of eight 7 millimetre long, 45° spaced, measuring electrodes 52 or 53. On either side of these measuring electrodes are eight 20 millimeter long, 45° spaced, shielding electrodes 54 and 56 or 55 and 57. The axial distance between the centre lines of the two flow sensors 48 and 50 is about 10 centimeters. The capacitance in the wellbore annulus sectors defined by pairs of two adjacent electrodes 52 or 53, is measured in the same way as for the void fraction measurement section 26. The gas velocity measurement is made by correlating versus time the capacitance measurement in two corresponding sectors in the annulus, one measurement being made by two adjacent electrodes 52 of the set 48 and the other being made by two corresponding electrodes 52 of the other set 50. By corresponding electrodes it is meant electrodes which are on the same generatrix (or generatrices) of the logging tool. The passage of gas bubbles through each flow sector give rise to rapid fluctuations in the capacitance measured by both flow sensors. These fluctuations are correlated as a function of time, in a known manner, to calculate the gas velocity in the considered flow sector. By multiplexing the potentials applied to the eight electrodes (as for the void fraction measurement), the electrostatic field can effectively be rotated in steps of 45°, allowing cross correlation estimates of the gas velocity to be obtained at eight discrete locations in the flow annulus. Thus, the flow annulus can be considered as being divided into eight sectors (as shown in FIG. 3 for the volume fraction measurement section), the gas velocity being measured in each sector.

Obviously, a non capacitance flow sensor could be used to determine the gas flow velocity, instead of the capacitance sensor 28. Other suitable sensors could be, for example, resistive, ultrasonic, or nuclear.

Figure 7:
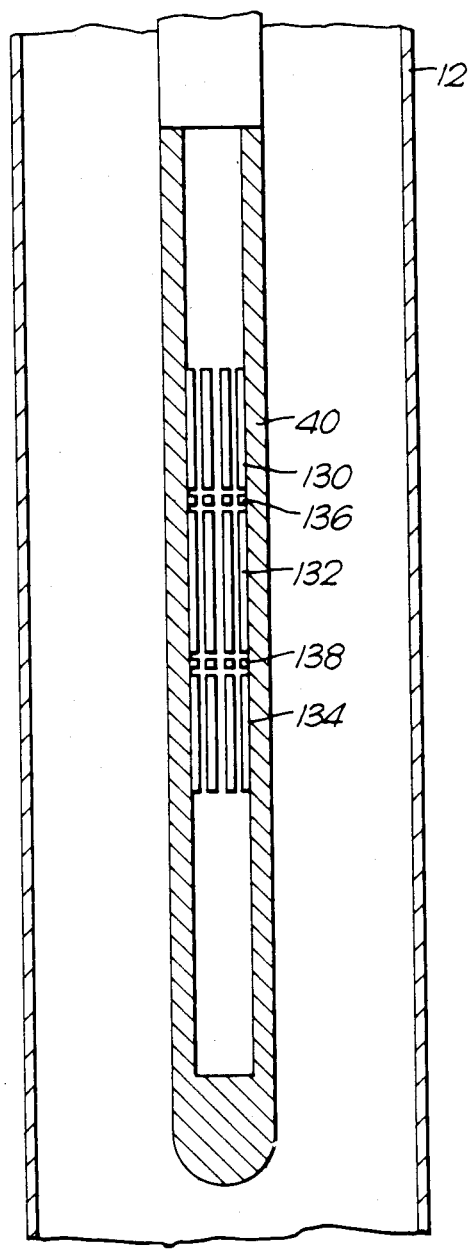
FIG. 7 shows schematically a second embodiment of the invention.

FIG. 7 represents schematically another embodiment of the invention in which the gas volume fraction measurement section and the gas velocity measurement section are combined together. The electrodes of the gas void fraction measurement section comprise three sets of eight, 45° spaced, electrode elements 130, 132 and 134. Between the two elements 130 and 132 is one set of eight, 45° spaced, electrodes 136 and between the two elements 132 and 134 is another set of eight, 45° spaced, electrodes 138. The gas void fraction measurement is made by the three elements 130, 132 and 134, three longitudinally aligned elements forming an electrode. By comparison with the embodiment of FIG. 1, one electrode 38 is composed of three elements 130, 132 and 134 aligned on the same generatrices. The electrodes 136 and 138 are the equivalent of electrodes 52 and 53 respectively in the embodiment of FIG. 1. When flow velocity measurements are made, the electrodes 130, 132 and 134 are used as guard electrodes and are therefore the equivalent of electrodes 54, 55, 56 and 57 of the embodiment of FIG. 1. Otherwise the structure of the two embodiments and the measurement methods are the same.

By combining the measured values of gas velocity and gas void fraction in each flow sector with a measurement of the pressure and temperature of the fluid at the location of the tool, it is possible to calculate the volume flow rate and mass flow rate of gas in each sector, the mass flow rate being obtained by multiplying the volume flow rate by the density of the gas (as a consequence, in the following description equations related to mass flow rate only are given). As a fact, the density d of the gas at the location of the logging tool is a function of the downhole temperature T and the downhole pressure p, both of which are measured with transducers 60 and 62. If the gas behaves as a perfect gas, then the downhole density d is given by;

$$d = p/rT$$

where r is the gas constant for the particular gas under consideration.

Let us now suppose that the gas void fraction in the i'th flow sector is $a_i$, the mean gas velocity in the i'th sector is $v_i$ and the cross sectional area in the i'th sector is A (all eight sectors have the same cross sectional area A). The mass flow rate $m_i$ of gas in the i'th sector is then given by;

$$m_i = A.d.a_i.v_i$$

The total mass flow rate m of gas past the logging tool is the sum of all the $m_i$ for all eight sectors of the borehole, i.e., $m = Ad(a_1.v_1 + a_2.v_2 + \ldots + a_8.v_8)$.

An alternative is to determine the mean gas void fraction by calculating the mean value a of the eight gas void fractions $a_i$ in the eight sectors and to determine the mean gas velocity by calculating the mean value v of the eight velocities $v_i$ in the eight sectors. Then the total volume flow rate and the total mass flow rate m of gas can be calculated, the latter being given by:

$$m = A.d.v.a$$

There is no need to describe any particular equipment to perform these calculations, which are straightforward. A microprocessor could advantageously be used.

The invention could also be used to measure the flow rate of any other phase such as water or solids distributed in separate particles or droplets in a continuous medium of a non-conducting fluid such as oil.

I claim:

1. A logging tool for use in a borehole for determining at least one characteristic of the discontinuous phase of a two-phase fluid circulating in said borehole around said logging tool, said logging tool having a substantially cylindrical shape and a longitudinal axis, the continuous phase of the fluid being electrically non-conducting, said logging tool comprising:
  (a) at least one set of at least three longitudinal electrodes extending parallel to said longitudinal axis of said tool and positioned and regularly spaced around said longitudinal axis;
  (b) means for producing an electric field and for obtaining an electric field pattern distributed essentially radially between said electrodes and the wall of said borehole facing said electrodes, said means being located around said electrodes;
  (c) means, extending on the outside of the tool, for substantially centralizing said tool in said borehole; and
  (d) means, connected to the electrodes, for measuring sequentially the capacitance between two adjacent electrodes for each pair of electrodes, said at least one characteristic of the discontinuous phase of said fluid being derived from said capacitance measurement.

2. The logging tool in accordance with claim 1 wherein said means for obtaining said electric field pattern comprises a cylindrical sleeve made of a dielectric material and located in contact and around said electrodes between said electrodes and said wall of said borehole.

3. The logging tool in accordance with claim 2 wherein the permittivity of said sleeve of dielectric material is chosen to be substantially equal to the permittivity of said continuous phase of said fluid.

4. The logging tool in accordance with claim 2 wherein said electrodes have a radius $r_1$ and said sleeve has a thickness $r_2$, and wherein the ratio $r_1/r_2$ is from about 0.58 to about 0.66.

5. The logging tool in accordance with claim 1 wherein said means for obtaining an electric field pattern comprises a centre body aligned with said longitudinal axis of said tool, and having ribs extending radially from said centre body between adjacent electrodes, said ribs being held at earth potential.

6. The logging tool in accordance with claim 5 further comprising insulating wedges located between said electrodes and said centre body.

7. The logging tool in accordance with claim 1, wherein said means for measuring sequentially the capacitance between two adjacent electrodes comprises means for establishing a known difference of potential V(t) between said two electrodes, all electrodes of the tool being held substantially at earth potential except one of the said two adjacent electrodes which is held at said potential V(t).

8. The logging tool in accordance with claim 1 wherein said at least one characteristic of said discontinuous phase is its volume fraction in said fluid.

9. The logging tool in accordance with claim 8 further comprising velocity means disposed near said electrodes and around said longitudinal axis of the tool for measuring the flow velocity of the discontinuous phase of said fluid flowing near said electrodes, said flow velocity measurement and said volume fraction being combined so as to derive the volume flow rate and/or the mass flow rate of said discontinuous phase of said fluid.

10. The logging tool in accordance with claim 9 wherein said one set of electrodes is a first set of electrodes used to derive said volume fraction of said discontinuous phase of said fluid and further comprising a second and a third identical set of electrodes located at a known distance from each other, the number of electrodes in said second and third sets being equal to the number of electrodes in said first set of electrodes, said electrodes of said first, said second and said third sets being disposed around said longitudinal axis of said tool in the same manner whereby one electrode in each set has a corresponding electrode in each of the two other sets aligned on the same generatrix of said tool, the capacitance measurement of one pair of electrodes of said second set being correlated with the capacitance measurement of the corresponding pair of electrodes of said third set so as to determine the flow velocity of said discontinuous phase of said fluid.

11. The logging tool in accordance with claim 10 wherein each electrode of said second and said third sets is comprised of a measuring element and a guard element on both sides aligned on a same generatrix of said tool, said guard element being held at earth potential and said measuring element being connected to said means for measuring sequentially the capacitance between two adjacent electrodes for each pair of electrodes.

12. The logging tool in accordance with claim 10 wherein each electrode of said first set is comprised of three elements aligned on a same generatrix of said tool, the first two consecutive elements being separated by an electrode of said second set and the second two consecutive elements being separated by an electrode of said third set.

13. The logging tool in accordance with claim 12 wherein the volume fraction measured with each pair of electrodes of said first set is combined with the flow velocity measured with the corresponding pair of electrodes of said second and third sets so as to derive the volume flow rate and/or the mass flow rate of the discontinuous phase of said fluid for each flow sector in said borehole corresponding to said pairs of electrodes.

14. The logging tool in accordance with claim 13 wherein the overall volume flow rate or mass flow rate of the discontinuous phase of said fluid is calculated as the mean value of respectively the volume flow rates or the mass flow rates determined in all the flow sectors.

15. The logging tool in accordance with claim 10 wherein the number of electrodes in each of said sets is eight.

16. The logging tool in accordance with claim 1 wherein said discontinuous phase is gas and said continuous phase is oil.

17. The logging tool in accordance with claim 1 wherein said discontinuous phase is water and said continuous phase is oil.

* * * * *